United States Patent [19]
Uchida

[11] Patent Number: 5,653,237
[45] Date of Patent: Aug. 5, 1997

[54] APPARATUS FOR MEASURING BIOLOGICAL SIGNAL

[75] Inventor: Keisuke Uchida, Tokyo, Japan

[73] Assignee: Nihon Kohden Corporation, Tokyo, Japan

[21] Appl. No.: 624,093

[22] Filed: Mar. 29, 1996

[30] Foreign Application Priority Data

Mar. 31, 1995 [JP] Japan .................................. 7-076891

[51] Int. Cl.⁶ .................................................. A61B 8/02
[52] U.S. Cl. .......................... 128/661.1; 128/661.08
[58] Field of Search ..................... 128/660.01, 660.02, 128/660.03, 661.04, 696, 700, 716, 653.1, 653.2, 695 R, 661.08, 661.09, 661.1

[56] References Cited

U.S. PATENT DOCUMENTS

| | | | |
|---|---|---|---|
| 4,582,068 | 4/1986 | Phillips et al. | 128/716 |
| 4,751,931 | 6/1988 | Briller et al. | 128/700 |
| 4,991,587 | 2/1991 | Blakeley et al. | 128/653.2 |

*Primary Examiner*—George Manuel
*Attorney, Agent, or Firm*—Sughrue, Mion, Zinn, Macpeak & Seas

[57] ABSTRACT

An apparatus for measuring biological signals includes: a whole function input unit for detecting a parameter representing a whole function of an organ of a body to be measured; a regional function input unit for detecting a parameter representing a regional function of the organ of the body; a conversion operation unit for outputting a conversion value while converting the parameter from the regional function input unit into a value representing the whole function; a comparison operation unit for receiving the parameter representing the whole function outputted from the whole function input unit and the conversion value outputted from the conversion operation unit and calculating and outputting a ratio between the parameter representing the whole function and the conversion value or a difference between the parameter representing the whole function and the conversion value; a display control unit for receiving the parameter representing the whole function and the conversion value or the ratio between the parameter representing the whole function and the conversion value and outputting the received data as X-Y graph data; and a monitor for displaying the parameter representing the whole function and the conversion value or the ratio between the parameter representing the whole function and the conversion value on X-Y graph.

3 Claims, 4 Drawing Sheets

APPARATUS FOR MEASURING BIOLOGICAL SIGNAL

BACKGROUND OF THE INVENTION

The invention relates to an apparatus for measuring biological signals that detect an abnormality by measuring a whole function and a regional function of an organ of the body.

When one detects the presence of a regional abnormality of such organs of the body as the heart and the lung, a conventional method employs an apparatus for measuring biological signals and measures a parameter representing the whole function of an organ of the body to be measured so that the presence of an abnormality can be judged from a subtle change of the parameter brought about by a regional abnormality, or detects an abnormal region by measuring a parameter representing a regional function of an organ of the body for all the required regions of the organ of the body.

Further, other conventional methods employ various special apparatuses for measuring biological signals to give a subject a detailed examination from the outset.

However, for detecting such subtle change of the parameter brought about by a regional abnormality by measuring the parameter representing the whole function of the organ of the body to be measured, highly sophisticated expertise or a great amount of experience is required. When part of the organ becomes abnormal, the other part of the organ tends to compensate for the function of such abnormal part of the organ, therefore no change of the parameter representing the whole function takes place unless such abnormality is significantly aggravated. As a result, the detection of an abnormality has been delayed in some examinations using the conventional methods.

Further, when measuring the parameter representing the regional function of the organ of the body, it is necessary to take samples of the same parameter from a great number of all other regions of the organ of the body to be measured. As a result, the examiner may overlook some detected regions, which in turn requires that the regions be reexamined, thus causing emotional and physical distress to the subject. Still further, this type of examination requires a large and expensive measuring apparatus, which in turn entails much time for preparations for measurements and hence makes this type of examination unsuitable as a simple examination for abnormality detection.

Moreover, when making a detailed examination from the outset, the subject is forced to endure emotional and physical strain.

SUMMARY OF THE INVENTION

The invention has been made in view of the aforementioned circumstances. The object of the invention is, therefore, to provide an apparatus for measuring biological signals that can detect the presence of an abnormality, which has simple construction, by measuring a whole function parameter and a regional function parameter of an organ of the body.

To achieve the above object, according to a first aspect of the invention, an apparatus for measuring biological signals includes: a first input means for detecting a parameter representing a whole function of an organ of a body to be measured; a second input means for detecting a parameter representing a regional function of the organ of the body; a conversion operation unit for outputting a value converted from the parameter of the second input means into a value representing the whole function; and a comparison operation unit for receiving the parameter representing the whole function output from the first input means and the converted value output from the conversion operation unit and calculating and outputting a ratio between the whole function parameter and the conversion value or a difference between the parameter and the conversion value.

According to a second aspect of the invention, an apparatus for measuring biological signals includes: a first input means for detecting a parameter representing a whole function of an organ of a body to be measured; a second input means for detecting a parameter representing a regional function of the organ of the body; a conversion operation unit for outputting a conversion value converted from the parameter of the second input means into a value representing the whole function; a display control means for receiving the parameter representing the whole function and the conversion value and outputting the received parameter and conversion value as X-Y graph data; and a display means for displaying the output from the display control means.

According to a third aspect of the invention, an apparatus for measuring biological signals that includes: a first ultrasound probe for transmitting and receiving an ultrasound signal for measuring a short-axis inner diameter of a heart; a second ultrasound probe for transmitting and receiving an ultrasound signal for measuring a blood flow velocity of blood ejected from the heart; an ECG (electrocardiogram) signal detection means for detecting an ECG signal to be used as a trigger signal for a single heart beat; a control means including a first calculation means, a second calculation means, and a comparison operation means, the first calculation means receiving the ultrasound signal for measurement of the short-axis inner diameter detected by the first ultrasound probe, and the ECG signal and calculating a first stroke volume based on the ultrasound signal for measurement of the short-axis inner diameter, the second calculation means receiving the ultrasound signal for measurement of the blood flow velocity detected by the second ultrasound probe and the ECG signal and calculating a second stroke volume at the same time as the first stroke volume calculating time from the ultrasound signal for measurement of the blood flow velocity, and the comparison operation means calculating a ratio between the first stroke volume and the second stroke volume; and a display means for displaying the first and the second stroke volumes output from the control means on X-Y graph.

The invention of the first aspect is characterized in that: the parameter representing the whole function of an organ of the body to be measured is detected by the first input means and the parameter representing the regional function of the organ of the body is detected by the second input means; the parameter detected by the second input means is output as a conversion value while converted into the parameter representing the whole function by the conversion operation unit; and either the ratio of the conversion value to the whole function parameter output from the first input means or the difference between the conversion value and the whole function parameter is calculated and outputted as calculated data.

The invention of the second aspect is characterized in that: the parameter representing the whole function of an organ of the body to be measured is detected by the first input means and the parameter representing the regional function of the organ of the body is detected by the second input means; the parameter detected by the second input means is output as a conversion value while converted into the parameter representing the whole function by the conversion operation unit; both the whole function parameter and the conversion value and the ratio between the whole function parameter and the conversion value is output to the display control unit, and displayed on the display means as X-Y graph data; and the display means displays the whole function parameter, the conversion value, or the ratio between the whole function parameter and the conversion value on the X-Y graph on the screen thereof.

The invention of the third aspect is characterized in that: ultrasound signals are transmitted and received by locating the first and the second ultrasound probe to the required positions and then measuring the short-axis inner diameter and blood flow velocity of the heart; further, the ECG signal to be used as a trigger signal for a single heart beat is detected; the control means receives the ultrasound signal for measurement of the short-axis inner diameter, the ultrasound signal for measurement of the blood flow velocity, and the ECG signal, calculates the first stroke volume based on the ultrasound signal for measurement of the short-axis inner diameter, calculates the second stroke volume at the same time as the first stroke volume calculating time from the ultrasound signal for measurement of the blood flow velocity, and calculates the ratio between the first and the second stroke volumes; and the monitor displays the first and the second stroke volumes outputted from the control means or the ratio between the first and the second stroke volumes on the X-Y graph.

DETAILED DESCRIPTION OF THE PREFERRED EMBODIMENTS

Figure 1:
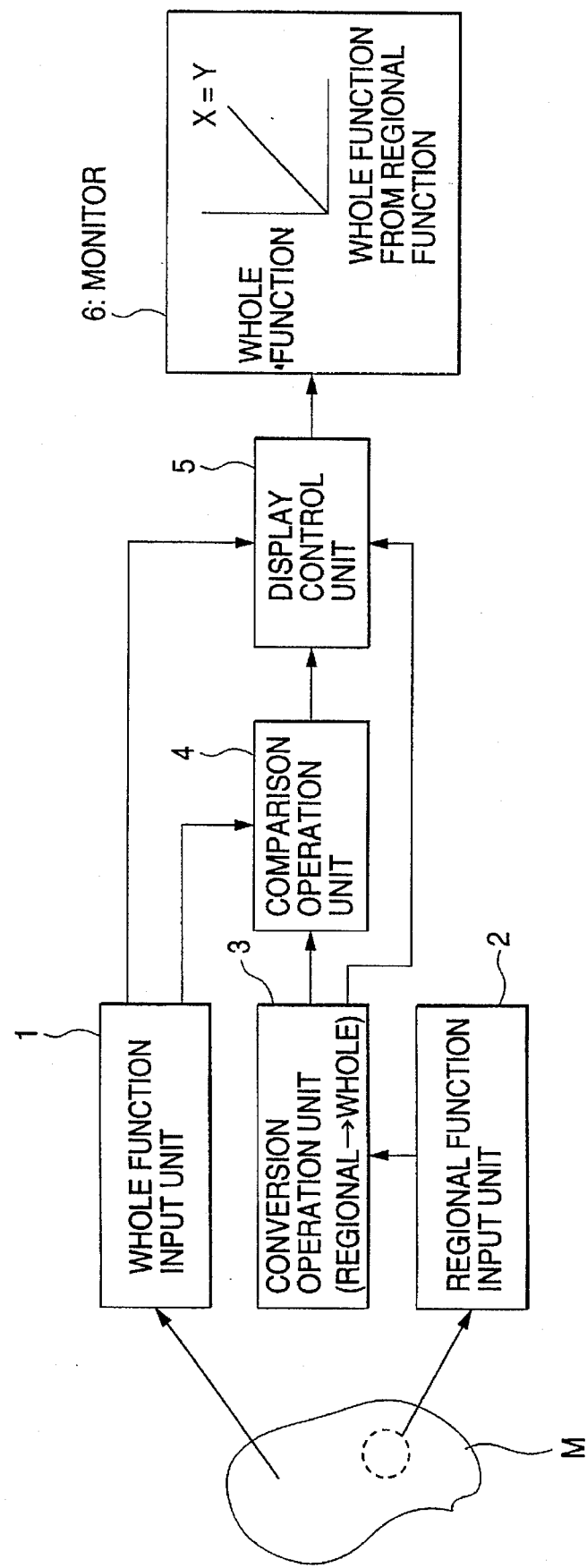
FIG. 1 is a block diagram showing a configuration of an apparatus for measuring biological signals of the invention.

Apparatuses for measuring biological signals, which are embodiments of the invention, will now be described with reference to the drawings. FIG. 1 is a block diagram showing a configuration of an embodiment of the invention.

In FIG. 1, reference character M denotes an organ of the body such as a heart; reference numeral 1 denotes a whole function input unit that detects a required biological signal representing the whole function of the organ of the body M as a parameter; and 2, a regional function input unit that detects a required biological signal representing a regional function of the organ of the body M as a parameter. Each of the whole function input unit 1 and the regional function input unit 2 has an electrode, a sensor or an ultrasound probe and an amplifier for amplifying the detected parameter, although not shown in the drawing. Reference numeral 3 denotes a conversion operation unit that receives the regional function parameter applied from the regional function input unit 2 and converts the received parameter into the parameter representing the whole function and outputs such parameter representing the whole function as a conversion parameter. Reference numeral 4 denotes a comparison operation unit that not only receives the whole function parameter applied from the whole function input unit 1 and the conversion parameter applied from the conversion operation unit 3 to calculate the ratio between both parameters but also exerts control over the entire part of the apparatus. The comparison operation unit 4 is constructed of, e.g., a CPU. Further, reference numeral 5 denotes a display control unit constructed of, e.g., a CPU. The display control unit 5 receives the parameter from the whole function input unit 1, the conversion parameter from the conversion operation unit 3, and the ratio between the whole function parameter and the conversion parameter applied from the comparison operation unit 4, converts the received data into X-Y graph data, outputs the converted X-Y graph data on a monitor 6 that is constructed of, e.g., a CRT or a liquid crystal display, displays the whole function parameter and the conversion parameter or displays the ratio between both parameters on X-Y graph. The aforementioned comparison operation unit 4 and the display control unit 5 may be constructed of, e.g., a single CPU as a control means.

In the aforementioned configuration, the electrode, the sensor, or the ultrasound probe is attached to an organ of the body of a subject to be examined or to a required region close to such organ of the body, and the required parameters are then detected by the whole function input unit 1 and the regional function input unit 2. The parameter detected by the whole function input unit 1 is fed to the comparison operation unit 4 and the display control unit 5.

On the other hand, the parameter detected by the regional function input unit 2 is fed to the conversion operation unit 3 and converted into the parameter of the whole function by the conversion operation unit 3. The conversion parameter is output to the comparison operation unit 4 and the display control unit 5.

The comparison operation unit 4 calculates the ratio of the whole function parameter to the conversion parameter which have been received, and outputs the calculated ratio to the display control unit 5. Receiving the parameter from the whole function input unit 1 and the conversion parameter from the conversion operation unit 3, the display control unit 5 either outputs these data as X-Y graph data or outputs to the monitor 6 the ratio of the whole function parameter to the conversion parameter output from the comparison operation unit 4 as X-Y graph data.

On the screen of the monitor 6, data that has been calculated based on the parameter representing the whole function measured by the whole function input unit 1 and the conversion data that has been calculated based on the parameter representing the regional function measured by the regional function input unit 2 and converted into the parameter representing the whole function are plotted as they change on a time-dependent basis, or the ratio between the whole function data and the regional function-based conversion data that has been converted into the parameter representing the whole function is displayed on the X-Y graph. In this case, if, e.g., all the parts are functioning normally, the same value is given to both parameters on the display screen, or the ratio between both parameters becomes "1" and is displayed on a straight line X=Y on the X-Y graph on the monitor screen, i.e., on a straight line drawn at an angle of 45° with respect to the horizontal axis of the X-Y graph.

If some regional function is abnormal, the regional function-based conversion data can be displayed at positions remote from the whole function data so as not to overlap on the whole function data. Therefore, the degree of such abnormality can be judged through how far the former is distanced from the latter. If, on the other hand, the ratio of the whole function data to the regional function-based conversion data is not equal to "1", the conversion data deviates from the X=Y line either upward or downward. Therefore, the presence of an abnormality can be found. If an abnormality is found, a detailed examination can be made using special examination apparatuses.

If the ratio of the whole function data to the regional function-based conversion data is indicated in the form of logarithm, the degree of an abnormality can be judged through how far the ratio is distanced from the normal value "0" since the logarithm for indicating that an organ is functioning normally is "0".

Further, one may also indicate the distance from the normal value "0" by taking a difference between the whole function data and the regional function-based conversion data.

Figure 2:
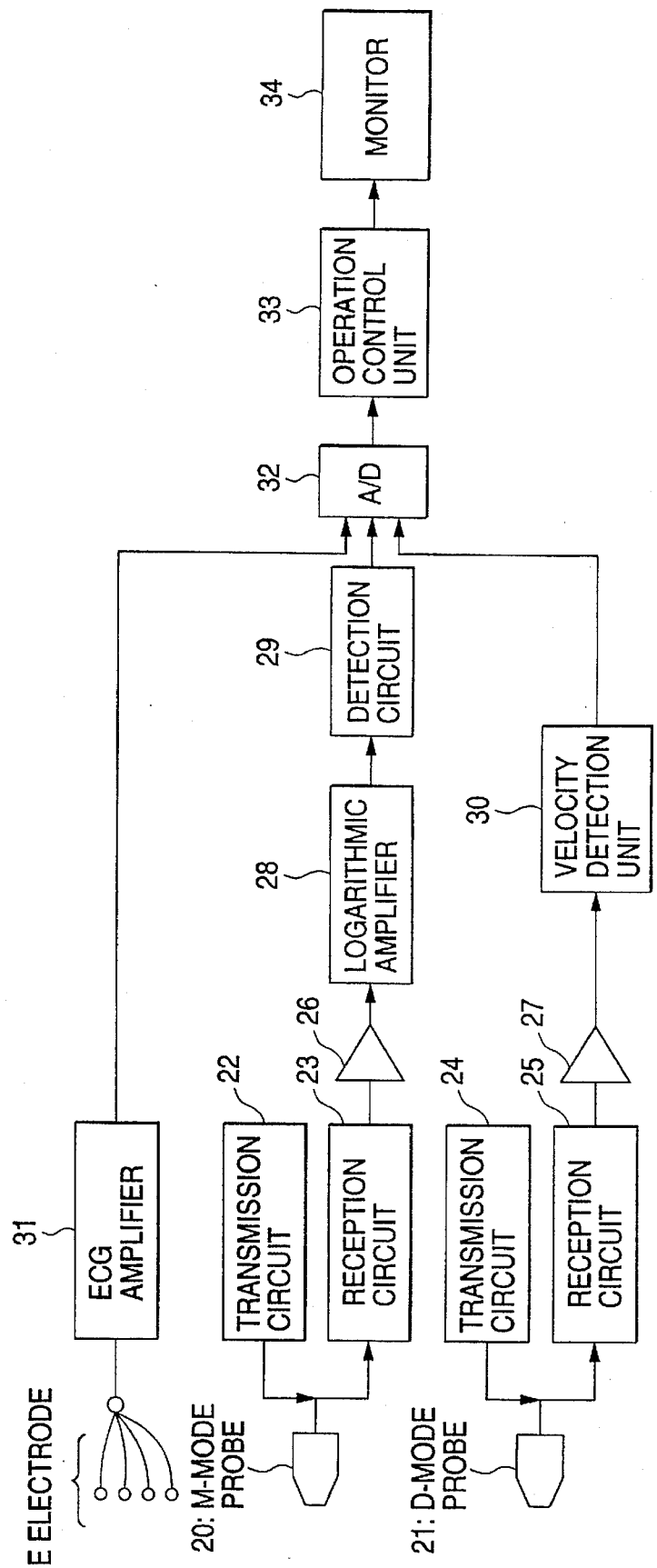
FIG. 2 is a block diagram of an applied example when the embodiment shown in FIG. 1 is applied to a heart.
Figure 3:
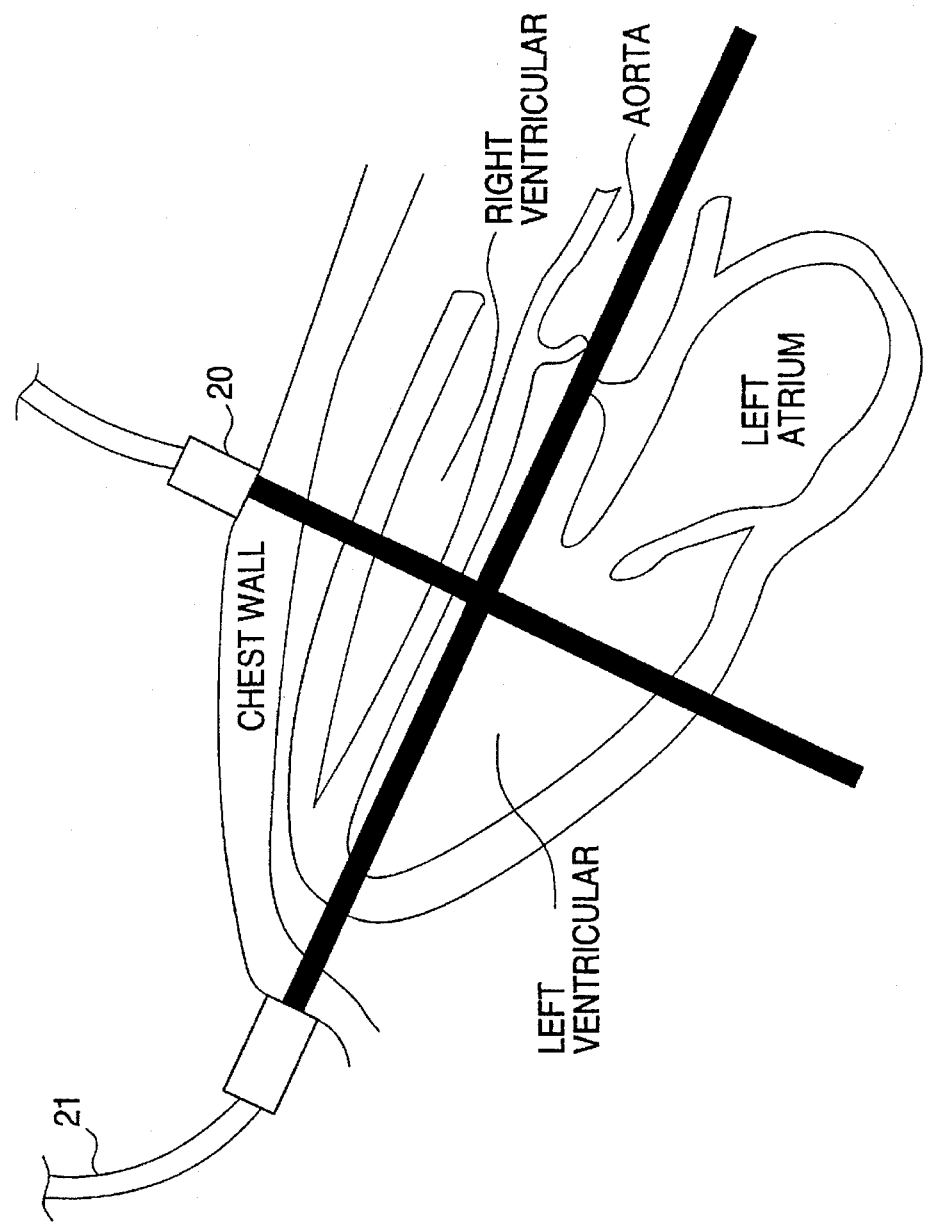
FIG. 3 is a diagram showing positions to which ultrasound probes are located in the applied example shown in FIG. 2.
Figure 4:
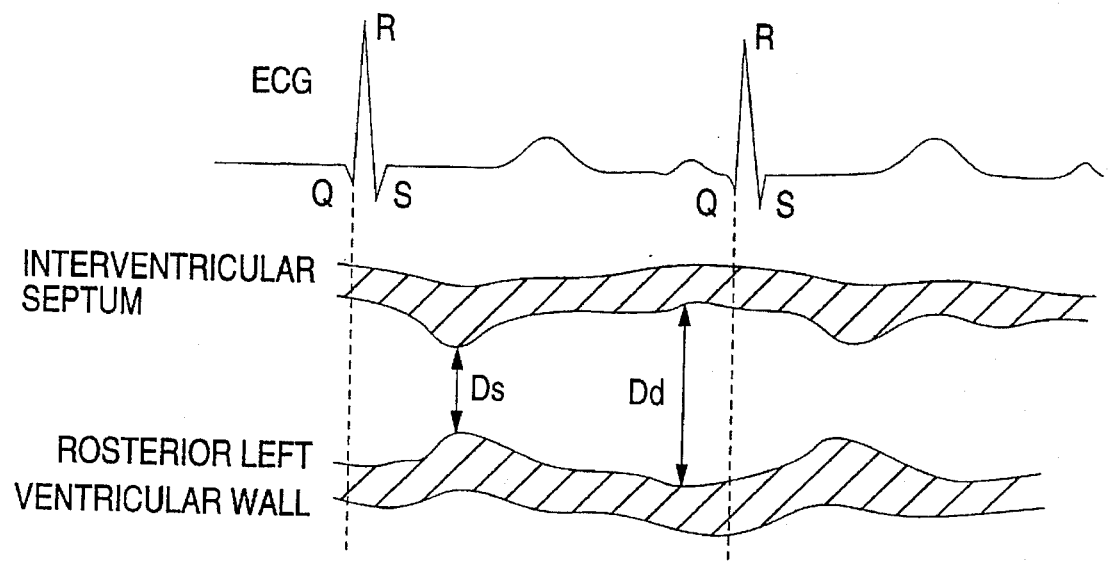
FIG. 4 is a diagram illustrative of measurement of a left ventricular short-axis inner diameter of the heart in the applied example shown in FIG. 2.
Figure 5:
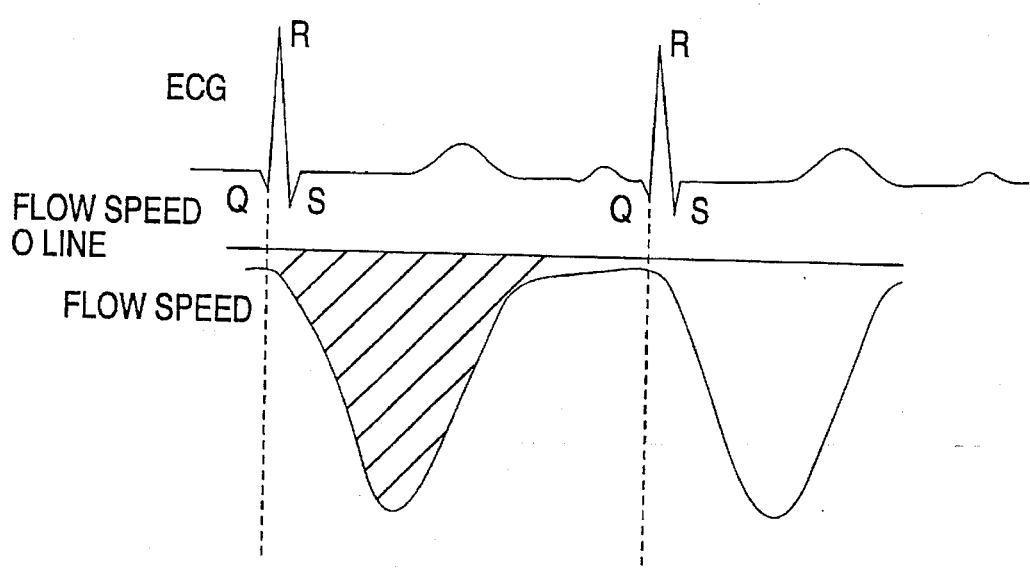
FIG. 5 is a diagram illustrative of measurement of a blood flow velocity of the heart in the applied example shown in FIG. 2.

An applied example of the aforementioned embodiment will be described with reference to FIGS. 2 to 5. FIG. 2 is a block diagram showing a configuration of an example in which the embodiment shown in FIG. 1 is applied to the detection of, e.g., the angina pectoris. FIG. 3 shows an example in which ultrasound probes are located at required regions in the applied example of FIG. 2. FIG. 4 shows an M-mode echocardiogram detected in FIG. 3. FIG. 5 shows a Doppler echocardiogram detected in FIG. 3.

This example is designed to not only calculate a stroke volume from blood flow velocity by measuring the blood flow velocity in an ultrasound Doppler mode as the parameter representing the whole function of an organ of the body, but also calculate a stroke volume from left ventricular short-axis inner diameter by measuring the left ventricular short-axis inner diameter in an ultrasound M-mode as the parameter representing the regional function of the organ of the body. The left ventricular short-axis inner diameter reflects movements of the posterior left ventricular wall and the interventricular septum.

In FIG. 2, reference numeral 20 denotes an M-mode ultrasound probe (hereinafter referred to as the "M-mode probe"); and 21, a Doppler mode ultrasound probe (hereinafter referred to as the "D-mode probe").

FIG. 3 shows an example in which the M-mode probe 20 and the D-mode probe 21 are arranged so that ultrasound signals are transmitted and received in the parasternal location (short-axis direction) and the apical location (long-axis direction) of the heart, respectively. Generally, the M-mode indicates time-dependent variations of an organ of the body, whereas the Doppler mode is designed to emit an ultrasound signal onto an object showing movement such as blood and to indicate time-dependent variations of the object, i.e., the blood flow velocity and the like, as frequency change with respect to a reference frequency.

In FIG. 3, the M-mode probe 20 and the D-mode probe 21 are located at the required positions of the chest wall, respectively. The M-mode probe 20 measures the left ventricular short-axis inner diameter of the heart, and the D-mode probe 21 measures the blood flow velocity of the left ventricular outflow tract caused by contraction of the heart.

Returning to FIG. 2, the M-mode probe 20 is connected to a transmission circuit 22 that transmits an ultrasound signal and a reception circuit 23 that receives the ultrasound signal reflected from the heart. Similarly, the D-mode probe 21 is connected to a transmission circuit 24 that transmits an ultrasound signal and a reception circuit 25 that receives the ultrasound signal reflected from the heart. The output terminal of the reception circuit 23 is connected to an amplifier 26, and the output terminal of the reception circuit 25 is connected to an amplifier 27.

Further, the output terminal of the amplifier 26 is connected to a logarithmic amplifier 28 that outputs the amplified signal in the form of an exponential signal. The output terminal of the logarithmic amplifier 28 is connected to a detection circuit 29 where the ultrasound signal is detected and demodulated. Still further, the output terminal of the amplifier 27 is connected to a velocity detection unit 30 that detects the blood flow velocity of, e.g., the aorta shown in FIG. 3.

Reference numeral 31 denotes an ECG amplifier that amplifies an ECG signal detected by a plurality of electrodes E attached to the chest. The ECG signal is traced so that a Q wave (FIG. 4) can be used as a trigger for calculating the stroke volume as will be described later.

The output terminals of the detection circuit 29, the velocity detection unit 30, and the ECG amplifier 31 are connected to an analog-to-digital converter 32, where the output signals from the components 29, 30, 31 are respectively converted into digital signals and output to an operation control unit 33 that is constructed of, e.g., a CPU. The operation control unit 33 has built-in storage elements such as a ROM and a RAM although not shown in the drawings. The ROM stores a control program in advance, and the RAM temporarily stores working data. The output terminal of the operation control unit 33 is connected to a monitor 34 that is constructed of, e.g., a CRT, a liquid crystal display, or the like.

As shown in FIG. 4, the operation control unit 33 detects from the ultrasound signal detected by the M-mode probe 20 per heart beat a left ventricular end-diastolic internal diameter Dd obtained at the time the blood in the heart is about to be ejected and a left ventricular end-systolic internal diameter Ds of the heart obtained after the blood has been ejected. From the detected data Dd and Ds, a left ventricular end-diastolic volume=$\{7.0/(2.4+Dd)\}\cdot Dd^3$ and a left ventricular end-systolic volume=$\{7.0/(2.4+Ds)\}\cdot Ds^3$ are calculated by a generally known Teichholz method. Then, stroke volume SVm can be obtained by calculating the difference between the two volumes from the following equation.

$$SVm=\{7.0/(2.4+Dd)\}\cdot Dd^3-\{7.0/(2.4+Ds)\}\cdot Ds^3 \qquad (1)$$

Further, as shown in FIG. 5, the operation control unit 33 integrates the wave form of the shaded left ventricular outflow tract blood flow velocity signal every heart beat with a Q wave in the ECG signal as a trigger. In order to calculate a stroke volume, it is necessary to multiply the integrated value by a cross-sectional area of the aorta. Since this method is applied to a stress test in which the subject is caused by exercise or drug is applied to the subject, calibration is made so that the stroke volume calculated from the left ventricular short-axis inner diameter before load equals the integrated value while assuming that the heart is functioning normally until loaded. That is, a coefficient $\alpha$ indicated in the following equation is calculated before stress, and the integrated value of the wave form of the left ventricular outflow tract blood flow velocity signal obtained at the time the stress has been applied is multiplied by the coefficient $\alpha$, so that the stroke volume at that moment can be calculated.

$$\alpha=SVm(\text{before load})\div\int_{t_2}^{t_1}V(t)dt \qquad (2)$$

$$SV(\text{after load})=\alpha\cdot\int_{t_{m-1}}^{t_m}V(t)dt \qquad (3)$$

In the above equations, t1 and t2 are the trigger time based on an arbitrary ECG signal before stress and the trigger time based on an ECG signal subsequent to such arbitrary ECG signal; tn and tn−1 are the trigger time based on an ECG signal (Q wave) of the same heart beat as the heart beat from which the stroke volume has been calculated in the M-mode after stress and the trigger time based on an ECG signal (Q wave) subsequent to such ECG signal; and V(t) is the left ventricular outflow tract blood flow velocity at a time t.

The operation control unit 33 outputs a single stroke volume calculated in the M-mode and a single stroke volume calculated in the Doppler mode for the same heart beat in this way as a time-dependent change on the X-Y graph, or calculates and outputs the ratio between both stroke volumes.

Reference numeral 34 denotes the monitor constructed of, e.g., a CRT or a liquid crystal display similar to that of the conventional example. The monitor 34 displays the time-dependent change between the single stroke volume of the Doppler mode and the single stroke volume of the M-mode generated from the operation control unit 33 or the ratio between both stroke volumes on the X-Y graph on the screen thereof.

In the aforementioned construction, the M-mode probe 20 for measuring the left ventricular short-axis inner diameter and the Doppler probe 21 for measuring the left ventricular outflow tract blood flow velocity are located at the required positions of the chest wall of the subject, respectively (FIG. 3), so that ultrasound signals are transmitted by the transmission circuits 22 and 24. Further, in order to select a trigger for a single heart beat to be calculated by the Doppler echocardiogram and the M-mode echocardiogram detected by the Doppler probe 21 and the M-mode probe 20, one arranges a plurality of electrodes E at the required positions of the chest of the subject and detects an ECG signal.

The ultrasound signal reflected by the left ventricle is detected by the M-mode probe 20, received by the reception circuit 23, amplified by the amplifier 26, converted into a required signal by the logarithmic amplifier 28, demodulated by the detection circuit 29, and converted into a digital signal by the analog-to-digital converter 32.

Further, the ultrasound signal reflected by the left ventricular outflow tract of the heart is detected by the Doppler probe 21, received by the reception circuit 25, and amplified by the amplifier 27. Then, a velocity component signal of the left ventricular outflow tract is detected by the velocity detection unit 30, and the detected signal is converted into a digital signal by the analog-to-digital converter 32.

Still further, the ECG signal detected by the electrodes E is amplified by the ECG amplifier 31, and converted into a digital signal by the analog-to-digital converter 32.

The ECG signal, the M-mode ultrasound signal, and the velocity component signal output from the analog-to-digital converter 32 are received by the operation control unit 33.

As shown in FIG. 4, the operation control unit 33 measures the left ventricular end-systolic internal diameter Ds and the left ventricular end-diastolic internal diameter Dd as the regional function parameters from the ultrasound signals detected by the M-mode probe 20 with, e.g., a Q wave of an ECG signal as a trigger. The operation control unit 33 further operates to convert the difference SVm between the left ventricular end-systolic volume and the left ventricular end-diastolic volume as a single stroke volume of the parameter representing the whole function based on equation (1).

In addition, the operation control unit 33 calculates the coefficient α before stress based on equation (2) from the ultrasound signal detected by the Doppler probe 21 with, e.g., a Q wave of an ECG signal shown in FIG. 5 as a trigger. The coefficient α is assumed to be the cross-sectional area of the left ventricular outflow tract. Moreover, the operation control unit 33 calculates a stroke volume after stress as the parameter represented whole function based on equation (3) from the same trigger time as that used to calculate the single stroke volume in the M-mode.

Still further, the operation control unit 33 outputs not only the single stroke volume converted into the parameter representing the whole function from the M-mode regional function parameter but also the single stroke volume calculated by the parameter representing the whole function obtained by the Doppler mode on the monitor 34 and presents the single stroke volume on the X-Y graph on the screen of the monitor 34. In this case, if the heart is functioning normally, the time-dependent output data are indicated as a time-dependent change so as to overlap one upon another on the X-Y graph. However, if the heart is functioning abnormally, the stroke volume value obtained in the M-mode is indicated remote from the stroke volume value obtained in the Doppler mode.

The operation control unit 33 also calculates the ratio of the single stroke volume calculated based on the M-mode to the single stroke volume calculated based on the Doppler mode and presents the calculated ratio on the X-Y graph on the screen of the monitor 34. In this case, by allowing the X=Y line to be displayed on the screen of the monitor 34 in advance, the degree of the abnormality can be judged through how far the calculated ratio is distanced from such line. In the case where the heart is functioning normally, the ratio becomes "1", which means that the ratio is superimposed upon the X=Y line.

While the left ventricular short-axis inner diameter of the heart is measured in the M-mode as the regional function parameter in the aforementioned example, the stroke volume can be calculated by measuring the left ventricular short-axis cross-sectional area by two dimensional echocardiogram.

While the stroke volume in the heart is taken as an example in the aforementioned applied example, the presence of an abnormality can be detected by similarly measuring required parameters for other organs of the body. For example, to measure the function of the lung, one may measure the breathing capacity as the whole function parameter, then measure the amount of ventilation in any bronchus as a regional function parameter, so that such amount of ventilation is converted into the breathing capacity measured as the whole function parameter. This helps detect a regional abnormality and harmonic abnormality of the lung.

As described in the foregoing, the apparatuses for measuring biological signals of the invention of the first and second aspects of the invention are characterized as facilitating the detection of an abnormality by comparing the data representing the whole function calculated from a regional function parameter of an organ of the body with the data calculated from a whole function parameter. In addition, the apparatuses of the invention are advantageous in detecting an abnormality more accurately than in the case of making measurements only with the whole function parameter of an organ of the body and more easily than in the case of making measurements at all the regions of an organ of the body.

The invention of the third aspect of the invention is characterized as calculating a stroke volume based on the blood flow velocity of the heart as the whole function parameter and a stroke volume based on the short-axis inner diameter of the heart as a regional function parameter from ultrasound signals, and as judging the presence of an abnormality in the heart by either displaying both stroke volumes or displaying the ratio between both stroke volumes. Therefore, the invention can provide the advantage of detecting an abnormality of the heart easily without giving stress or spiritual burden to the subject.

What is claimed is:

1. An apparatus for measuring biological signals, comprising:

first input means for detecting a parameter representing a whole function of an organ of a body to be measured;

second input means for detecting a parameter representing a regional function of the organ of the body;

a conversion operation unit for converting said parameter output from said second input means into a conversion value representing the whole function and for outputting said conversion value; and a comparison operation unit for receiving said parameter representing the whole function output from said first input means and said conversion value output from said conversion operation unit and for calculating and outputting one of a ratio between said parameter and said conversion value, and a difference between said parameter and said conversion value.

2. An apparatus for measuring biological signals, comprising:

first input means for detecting a parameter representing a whole function of an organ of a body to be measured;

second input means for detecting a parameter representing a regional function of the organ of the body;

conversion operation unit for converting said parameter output from said second input means into a conversion value representing the whole function and for outputting said conversion value;

display control means for receiving said parameter representing said whole function and said conversion value and for outputting said parameter and said conversion value as X-Y graph data; and display means for displaying said graph data output from said display control means.

3. An apparatus for measuring biological signals, comprising:

a first ultrasound probe for transmitting and receiving an ultrasound signal for measuring a short-axis inner diameter of a heart;

a second ultrasound probe for transmitting and receiving an ultrasound signal for measuring a blood flow velocity of blood ejecting from the heart;

ECG signal detection means for detecting an ECG signal to be used as a trigger signal for a single heart beat;

control means, including first calculation means, second calculation means, and control operation means, said first calculation means receiving said ultrasound signal for measurement of said short-axis inner diameter detected by said first ultrasound probe, said ultrasound signal for measurement of said blood flow velocity detected by said second ultrasound probe, and said ECG signal, and calculating a first stroke volume based on said ultrasound signal for measurement of said short-axis inner diameter, said second calculation means calculating a second stroke volume, at the same time that said first stroke volume is being calculated, from said ultrasound signal for measurement of said blood flow velocity, said comparison operation means calculating and outputting a ratio between said first stroke volume and said second stroke volume; and display means for displaying said first stroke volume and said second stroke volume output from said control means on an X-Y graph.

* * * * *